Figure 1:
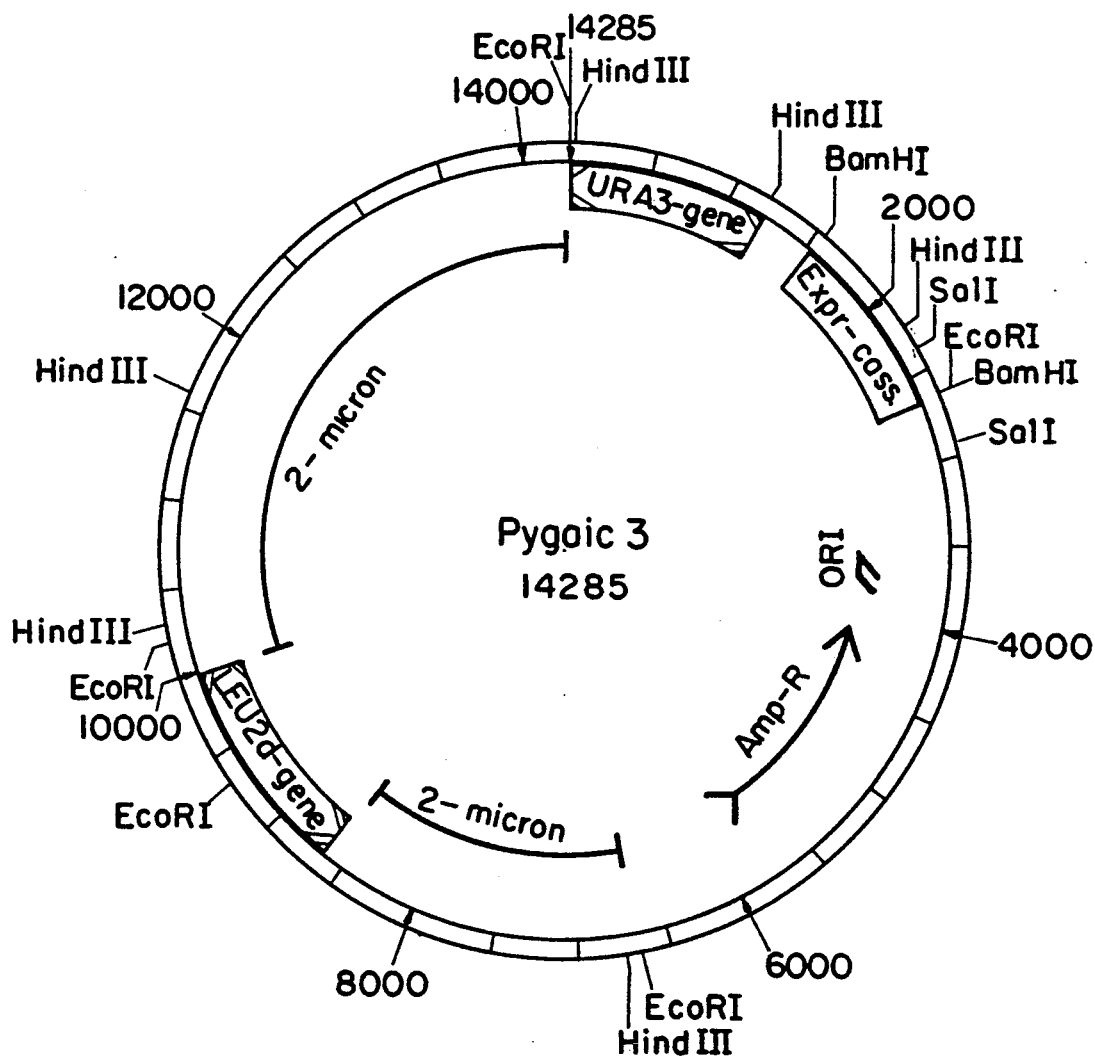

United States Patent [19]
Jonassen et al.

[11] Patent Number: 5,202,415
[45] Date of Patent: Apr. 13, 1993

[54] INSULIN PRECURSORS

[75] Inventors: Ib Jonassen, Valby; Ib G. Clausen, Charlottenlund; Einer B. Jensen, Virum; Allan Svendsen, Birkerod, all of Denmark

[73] Assignee: Novo Nordisk A/S, Bagsvaerd, Denmark

[21] Appl. No.: 623,739

[22] PCT Filed: Jun. 19, 1989

[86] PCT No.: PCT/DK89/00152
§ 371 Date: Dec. 13, 1990
§ 102(e) Date: Dec. 13, 1990

[87] PCT Pub. No.: WO89/12647
PCT Pub. Date: Dec. 28, 1989

[30] Foreign Application Priority Data

Jun. 20, 1988 [DK] Denmark ............................ 3361/88

[51] Int. Cl.⁵ ..................... A61K 37/02; A61K 37/26; C07K 5/00
[52] U.S. Cl. ........................................ 530/303; 514/3; 514/4
[58] Field of Search .......................... 514/3, 4; 530/303

[56] References Cited

U.S. PATENT DOCUMENTS 4,430,266 2/1984 Frank ................................. 530/303

FOREIGN PATENT DOCUMENTS 0195691 9/1986 European Pat. Off. .
8802005 3/1988 World Int. Prop. O. .

OTHER PUBLICATIONS

Dayhoff et al. Atlas of Protein Sequence and Structure, vol. 5 (1972) 89–99.
Rudinger, Peptide Hormones (Ja Parsons ed 1976) 1–6.

*Primary Examiner*—Merrell C. Cashinon, Jr.
*Assistant Examiner*—B. Celsa
*Attorney, Agent, or Firm*—Dann, Dorfman, Herrell and Skillman

[57] ABSTRACT

Insulin precursors characterized by the amino acid sequence $B(1-29)-X_1-X_2-Y_2-Y_1-A(1-21)$, wherein $B(1-29)$ are the 29 first amino acid residues of the B chain of human insulin starting from the N-terminus, $A(1-21)$ are the 21 amino acid residues of the A chain of human insulin, $X_1$ represents a peptide bond or one or more arbitrary amino acid residues, $X_2$ represents Glu or Asp, and $Y_1$ and $Y_2$ each represents Lys or Arg, the positions A6 and A11, A7 and B7 and A20 and B19, respectively, are connected through sulphur bridges, and, if desired, one or more of the amino acid residues of the chains $B(1-29)$ and $A(1-21)$ are substituted by another amino acid residue, are provided. The insulin precursors are prepared by culturing a yeast strain transformed with a replicable expression vehicle comprising a DNA sequence encoding an insulin precursor of the above formula in a suitable medium and isolating the insulin precursor thus formed from the culture medium. The insulin precursors can be converted into human insulin or insulin analogues by enzymatic treatment in a manner known per se.

6 Claims, 2 Drawing Sheets

INSULIN PRECURSORS

TECHNICAL FIELD

The present invention relates to novel propeptides More specifically, the invention relates to novel insulin precursors which can be used in the preparation of human insulin or insulins showing inherent protracted action or accelerated action. Moreover, the invention relates to DNA sequences coding for said insulin precursors as well as a process for the preparation of such precursors and to a process for the preparation of human insulin or insulin analogues.

BACKGROUND ART

In severe or chronic cases the disease of Diabetes is usually treated with injection preparations containing insulin, e.g. porcine insulin, bovine insulin or human insulin.

A number of different processes for the biosynthetic production of human insulin are known. Common to all of them is that the DNA strand coding for either the entire proinsulin, a modified form hereof or for the A and B chain separately is inserted into a replicable plasmid containing a suitable promoter. By transforming this system into a given host organism a product can be produced which can be converted into authentic human insulin in a manner known per se, cf. e.g. EP B1 85,083 or EP B1 88,117.

Some known processes for biosynthesis of proinsulin or similar insulin precursors and there conversion into insulin are described below.

Proinsulin may be prepared biosynthetically by using the method disclosed in the specification of European patent application No. 121,884. In this method the gene coding for proinsulin is inserted into a yeast strain and after culturing such transformed yeast strain proinsulin can be isolated from the culture medium. Hereafter, proinsulin can be converted into insulin in a manner known per se. Yields of proinsulin obtained by this method are, however, unsatisfactory low for commercial production.

Insulin precursors of the formula B-X-A wherein B and A represent the B and A chain, respectively, of human insulin and X represents a polypeptide comprising at least 2 amino acid residues, preferably from 6 to 35 amino acid residues, are known from the specification of Danish patent application No. 5284/87. The precursors can be enzymatically digested into human insulin by treatment with trypsin and carboxypeptidase B in the presence of certain metal ions.

European patent application No. 195,691 discloses closely related insulin precursors of the formula B-X-Y-A wherein B and A represent the B and A chain, respectively, of human insulin, cross-linked through sulphur bridges as in human insulin, and X and Y each represents a lysine or arginine residue, as well as the preparation of said precursors. These precursors can be enzymatically digested into human insulin by treatment with trypsin and carboxypeptidase B. Moreover, said precursors can undergo tryptic digestion into des-B30-insulin; however, a considerable amount of $A_o$Arg-des(B30)-insulin is formed which only slowly undergoes further digestion.

It is an object of the invention to provide novel insulin precursors which are generated in high yields in yeast and which furthermore can be converted into human insulin or insulin analogues with minimal formation of undesired by-products.

The insulin precursors of the invention are characterized by the following amino acid sequence

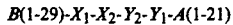

$$B(1\text{-}29)\text{-}X_1\text{-}X_2\text{-}Y_2\text{-}Y_1\text{-}A(1\text{-}21)$$

wherein B(1-29) are the 29 first amino acid residues of the B chain of human insulin starting from the N-terminus, A(1-21) are the 21 amino acid residues of the A chain of human insulin, $X_1$ represents a peptide bond or one or more arbitrary amino acid residues, $X_2$ represents Glu or Asp, and $Y_1$ and $Y_2$ each represents Lys or Arg, the positions A6 and A11, A7 and B7, and A20 and B19, respectively, are connected through sulphur bridges, and, if desired, one or more of the amino acid residues of the chains B(1-29) and A(1-21) are substituted by another amino acid residue.

The invention is based on the surprising recognition that the above insulin precursors are either generated in an extremely high yield as compared with the compound B-Lys-Arg-A known from European patent application No. 121,884 or that when these precursors are digested by trypsin des-B(30)-insulin is obtained in high yields with no or very little formation of $A_o$-Arg-des-B(30)-insulin and $A_o$-Lys-des-B(30)insulin or both.

It is preferred that $X_1$ represents a peptid bond or one amino acid residue.

Preferred precursors of the invention are represented by the formulas B(1-29)-Asp-Lys-Arg-A(1-21) and B(1-29)-Glu-Lys-Arg-A(1-21).

Des-B(30)-insulin can be converted into e.g. human insulin by enzymatically catalysed semisynthetic processes in a manner known per se.

The precursors may also be converted into human insulin by the transpeptidation method e.g. as described in U.S. Pat. No. 4,343,898.

Insulins in which one or more of the amino acid residues in the B(1-29) and A(1-21) chains are substituted by another amino acid residue may e.g. be the insulin derivatives showing protracted action and disclosed in the specification of international patent application WO 86/05497. In said insulin derivatives showing protracted action one or more of the amino acid residues of positions A4, A17, B13 and B21 are substituted by an amino acid residue having an uncharged side chain, e.g. an alkyl ester or an amid. Further insulin analogues which can be prepared according to the present invention are such insulins as described in European patent application Nos. 194,864 and 214,826.

The insulin precursors of the invention can be prepared by expressing a DNA sequence encoding an insulin precursor of the invention in a suitable expression system, preferably a yeast expression system.

The DNA sequence encoding the insulin precursors of the invention can be prepared from a DNA sequence encoding an insulin precursor B(1-30)-Lys-Arg-A(1-21) by in vitro mutagenesis or by oligonucleotide synthesis of the entire DNA sequence.

The invention is also related to a process in which a yeast strain transformed by a replicable expression vehicle comprising a DNA sequence encoding the insulin precursor with the above formula is cultured in a suitable culture medium, and then the precursor thus formed, optionally after isolation thereof, is converted into des-B(30)-insulin by tryptic digestion.

The present invention is furthermore related to a method for the preparation of human insulin or insulin analogues by which method a yeast strain transformed with a replicable expression vehicle comprising a DNA sequence encoding an insulin precursor of the above formula is cultured in a suitable culture medium whereupon the precursor thus formed is converted into human insulin or insulin analogues by known means.

To achieve secretion to the culture medium, the DNA sequence encoding the insulin precursors can be fused to another DNA sequence encoding a signal peptide functional in yeast. Secretion can be achieved by insertion in the expression vehicle of the yeast MFα1-leader sequence (Kurjan & Herskowitz, Cell 30, 933–943, 1982) or parts thereof. A preferred construction uses the DNA sequence encoding the entire MFα1-leader sequence including the dibasic site LysArg but excluding Glu-Ala-Glu-Ala which is the substrate for the yeast protease DPAP (dipeptidyl aminopeptidase). In that way, an efficient secretion of insulin precursors having the correct N-terminal is achieved. Other suitable leader sequences are synthetic yeast leader peptides as described in WO 89/02463.

The expression of the desired DNA sequence is under the control of a DNA sequence which is a promoter for transcription correctly positioned in relation to the DNA sequence being expressed. In the preferred embodiment the GAPDH (glyceraldehyd-3-phosphate-dehydrogenase) promoter is used. As the terminator of the transcription the terminator sequence of the MFα-1-gene is used.

The invention is further illustrated with reference to the drawings in which gion. The expression cassette is constructed using standard techniques.

2. Preparation of DNA Sequences Encoding a Secretion Signal and Modified Insulin Precursors DNA sequences encoding insulin precursors of the invention were constructed from the expression cassette described above. The method employed was "site directed in vitro mutagenesis" which is described by Zoller & Smith, DNA, Vol. 3, No. 6, 479–488 (1984). The method is briefly described in the following and is described in detail in Example 1. Isolated from the expression plasmid the insulin precursor sequence is inserted into a single-stranded, circular M13 bacteriophage vector. To the single-stranded vector, a chemically synthesized complementary DNA-strand is annealed. The DNA-strand contains the desired sequence surrounded by sequences completely homologous to insulin sequences on the circular DNA. In vitro, the primer is then extended in the entire length of the circular genom biochemically using Klenow polymerase. Hereby a double-stranded molecule is obtained, one strain of which has the desired sequence. This strand gives rise to single-stranded phages which are grown in E. coli. In this way double-stranded DNA with the desired sequence is obtained. From this double-stranded DNA, a restriction fragment can be isolated and reinserted into the expression vector. In this way insulin precursor sequences were constructed which are shown below together with the primers which were used in the preparation.

H3: B(1–29)-LeuAspLysArg-A(1–21)
    5'CAACAATACCTCTCTTGTCCAACTTTGGAGTG3'

H5: B(1–29)-AspLysArg-A(1–21)
    5'CAACAATACCTCTCTTGTCCTTTGGAGTG3'

H6: B(1–29)-GluLysArg-A(1–21)
    5'CAACAATACCTCTCTTTTCCTTTGGAGTG3'

H8: B(1–29)-LeuGluLysArg-A(1–21)
    5'CAACAATACCTCTCTTTTCCAACTTTGGAGTG3'

Figure 2:
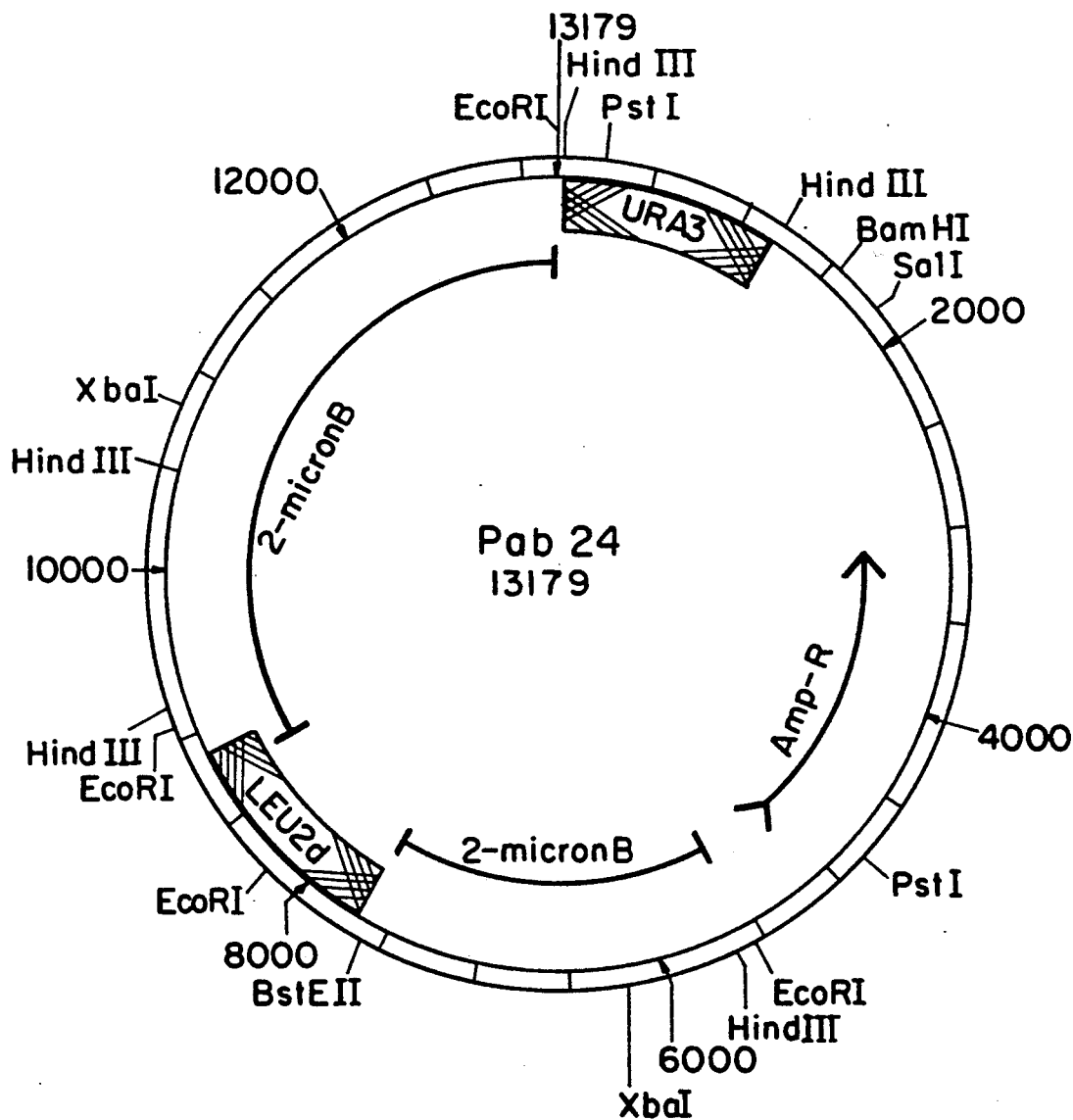

FIG. 1 shows the plasmid pYGAIC3 and
FIG. 2 the yeast vector pAB24.

The following examples further illustrate the invention.

1. Description of a DNA Sequence Encoding a Transcription Signal, a Secretion Signal and the Insulin Precursor B-LysArg-A The expression cassette which is contained in the BamHI restriction fragment on the plasmid pYGAIC3 as shown in FIG. 1 has a length of 1112 base pairs and contains essentially the following (listed in succession starting from the 5'-end): The GAPDH promotor (Travis et al., J. Biol. Chem., 260, 4384–4389, 1985) followed by the coding region consisting of: The 83 N-terminal amino acids of the MFα1-leader sequence encoded by the wild-type yeast DNA-sequence as described by Kurjan & Herskowitz (reference given above) followed by the two codons AAA and AGA encoding Lys and Arg and again followed by the coding region for B(1–30)-LysArg-A(1–2I) which is a synthetically constructed gene using preferred yeast codons. After two stop-codons a SalI restriction site is positioned, and the remaining part of the sequence consists of MFα1-sequences containing the terminator re- Experimental The region between the B and A chains of the insulin precursors can be modified by in vitro mutagenesis, the principles of which are described in Zoller & Smith, DNA, Vol. 3, No. 6, 479–488 (1984). In this example a slightly modified method of the Zoller & Smith protocol is used.

EXAMPLE 1

Construction of an Expression Plasmid which can be used in the Production of B(1-29)-GluLysArg-A(1-21) (=H6)

Isolation of Restriction Fragment Containing the Expression Cassette

The expression cassette which is contained in the expression plasmid pYGAIC3 shown in FIG. 1 in a BamHI restriction fragment was isolated as follows:

The expression plasmid was incubated with the restriction endonuclease BamHI. The conditions were as follows: 20 μg of plasmid, 50 units of BamHI, 100 mM NaCl, 50 mM Tris-HCl, pH 7.5, 10 mM MgCl$_2$, and 1 mM DTT in a reaction volume of 100 μliters. The temperature was 37° C. and the reaction time 2 hours. The two DNA fragments were separated on a 1% low-melting agarose gel, and the desired fragment was isolated by standard procedures.

Ligation to the Vector M13mp18

The isolated restriction fragment was ligated to the bacteriophage vector M13mp18 cut with the restriction endonuclease BamHI in the following reaction mixture: Fragment 0.2 µg, vector 0.02 µg, 50 mM Tris-HCl, pH 7.4, 10 mM MgCl$_2$, 10 mM DTT, and 1 mM ATP in a volume of 20 µliters. 5 µliters of this mixture were transformed into the E. coli strain JM101 by standard procedures. The presence of fragment in the vector as well as the orientation of the fragment was determined by restriction enzyme mapping on double-stranded M13-DNA isolated from the transformants.

Isolation of Single-Stranded (SS) DNA (Template)

From the transformant described above ss-DNA was isolated according to the method described by Messing & Vieira in Gene, 19, 269-276 (1982).

5'-Phosphorylation of the Mutagenisation Primer

The mutagenisation primer was phosphorylated in the 5'-end in a 30 µliters reaction volume containing 70 mM Tris-HCl, pH 7.0, 10 mM MgCl$_2$, 5 mM DTT, 1 mM ATP, 100 pmol oligonucleotide and 3.6 units of T4 polynucleotide kinase. The reaction was carried out for 30 min. at 37° C. Then, the enzyme was inactivated by incubating the mixture for 10 min. at 65° C.

Annealing of Template and Mutagenisation Primer

Annealing of template and primer was carried out in a 10 µliters volume containing 0.5 pmol template, 4 pmol primer, 20 mM Tris-HCl, pH 7.5, 10 mM MgCl$_2$, 50 mM NaCl and 1 mM DTT by heating to 65° C. for 10 min. and cooling afterwards to 0° C.

Extension/Ligation Reaction

To the reaction mixture formed above 10 µliters of the following mixture were added: 0.3 mM dATP, 0.3 mM dCTP, 0.3 mM dGTP, 0.3 mM TTP, 1 mM ATP, 20 mM Tris-HCl, pH 7 5, 10 mM MgCl$_2$, 10 mM DTT, 3 units of T4 DNA ligase and 2.5 units of Klenow polymerase.

Then, the reaction was carried out for 16 hours at 16° C.

Transformation of JM101

The reaction mixture formed above was transformed in various dilutions into CaCl$_2$-treated E. coli JM101 cells using standard techniques and plated in 2×YT top agar on 2×YT agar plates. (2×YT Tryptone 16 g/liter, yeast extract 10 g/liter, NaCl 5 g/liter. 2×YT top, agar=2×YT with 0.4% agarose added and heated under pressure. 2×YT agar plates=2×YT with 2% agar added and heated under pressure. The plates were incubated at 37° C. overnight.

Identification of Positive Clones

The method used was plaque-lift hybridisation which is described in the following: a nitrocellulose-filter was placed on a plate with a suitable plaque-density so that the filter was wetted with liquid from the plate. The filter was then bathed in the following solutions: 1.5M NaCl, 0.5M NaOH for 30 sec., 1.5M NaCl, 0.5M Tris-HCl, pH 8.0 for 1 min., 2×SSC (0.3M NaCl, 0.03M sodium citrate) till later drying. The filter was then dried on 3MM paper and baked for at least 2 hours at 80° C. in a vacuum oven.

5'-$^{32}$P-Labelling of the Mutagenisation Primer

The mutagenisation primer with the sequence 5'CAACAATACCTCTCTTTTCCTTTGGAGTG3' was labelled radioactively at the 5'-end in a 50 µliters reaction volume containing 70 mM Tris-HCl, pH 7.5, 10 mM MglC$_2$, 5 mM DTT 10 pmol oligonucleotide and 50 pmol γ-$^{32}$P-ATP. The reagents were heated to 37° C. and the reaction was initiated by addition of 3.5 units of T4 polynucleotide kinase. The mixture was incubated at 37° C. for 30 min. and then the enzyme was inactivated by heating to 100° C. for 3 min.

Hybridizing with Radioactive Primer to Nitrocellulose-Filters

The dried filters were prehybridized for 2 hours at 65° C. in 50 ml of the following solution: 0.9M NaCl, 0.09M sodium citrate, 0.2% bovine-serum albumin, 0.2% Ficoll, 0.2% polyvinylpyrrolidon, 0.2% sodium-dodecylsulphate (SDS) and 50 µg/ml salmon-sperm DNA. Then, one half of the labelling reaction mixture was added as probe to 15 ml of fresh prehybridization buffer, and the filter was bathed herein overnight at 37° C. with gentle shaking. After hybridization, the filter was washed at 30° C. 3 times for each 15 min. in 0.3M NaCl, 0.03M sodium citrate and autoradiographed. After wash in the same buffer at 60° C., and another autoradiography, plaques containing DNA sequences complementary to the mutagenisation primer were identified. The frequence of mutagenesis was 43%.

Purification of Double-Stranded M13-Phage DNA

After plating of a positive clone and another identification of positive plaques by hybridization one of the positive clones was used for infection of the E. coli strain JM101. Approximately 10$^8$ phages and 5 colonies of JM101 were grown for 5 hours in a 5 ml 2×YT medium. Then, double-stranded, circular DNA was purified from the cell pellet according to a method described by Birnboim & Doly, Nucleic Acids Res., 2, 1513 (1979).

Isolation of a Restriction Fragment Containing a Modified B-A-Link

The DNA preparation (appr. 5 µg) isolated above was digested with 10 units of the restriction endonuclease BamHI in 60 µliters of 100 mM NaCl, 50 mM Tris-HCl, pH 7.5, 10 mM MgCl$_2$, and 1 mM DTT for 2 hours at 37° C. The DNA products were separated by electrophoresis on an agarose-gel, and the desired fragment was purified from the gel by standard technique.

Ligation to the Yeast Vector pAB24

The isolated restriction fragment was ligated to the Yeast vector pAB24 shown in FIG. 2 cut with the restriction endonuclease BamHI in the following reaction mixture: Fragment 0.2 µg, vector 0,02 µg, 50 mM Tris-HCl, pH 7.4, 10 mM MgCl$_2$, 10 mM DTT, 1 mM ATP in a volume of 20 µliters. 5 µliters of this reaction mixture was used for transformation of the E. coli strain MC1061, in which the modified expression plasmid was identified and progagated. The plasmid was designated pYGAB-H6-A and had the same sequence as pYGAIC3, except for the altered region.

Transformation of Yeast

Transformation of the expression plasmid into the yeast strain *Saccharomyces cerevisiae* JC482ΔpepΔLeu cir° (α, his4, ura3, leu2, cir°) was carried out as described by H. Ito et al , J. Bact., Vol. 153, No. 1, 163–168 (1983). The transformed cells were plated on SC-ura medium (0.7% Yeast Nitrogen Base, 2.0% glucose, 0.5% casamino acids, 2.0% agar) for selection of plasmid containing cells.

EXAMPLE 2

Construction of an Expression Plasmid which can be used in the Production of B(1-29)-LeuAspLysArg-A(1-21) (=H3)

The procedure used was the same as described in example 1, except that the mutagenisation primer had the sequence 5'CAACAATACCTCTCTTGT-CCAACTTTGGAGTG3' and that the washing temperature after hybridization was 63° C. The final plasmid was designated pYGAB-H3-A and had the same sequence as pYGAIC3, except for the modified part.

EXAMPLE 3

Construction of an Expression Plasmid which can be used in the Production of B(1-29)-AspLysArg-A(1-21) (=H5)

The procedure used was the same as described in example 1, except that the mutagenisation primer had the sequence 5'CAACAA-TACCTCTCTTGTCCTTTGGAGTG3', and that the washing temperature after hybridization was 61° C. The final plasmid was designated pYGAB-H5-A and had the same sequence as pYGAIC3, except for the modified part.

EXAMPLE 4

Construction of an Expression Plasmid which can be used in the Production of B(1-29)-LeuGluLysArg-A(1-21) (=H8)

The procedure used was the same as described in example 1, except that the mutagenisation primer had the sequence 5'CAACAATACCTCTCTTTT-CCAACTTTGGAGTG3', and that the washing temperature after hybridization was 63° C. The final plasmid was designated pYGAB-H8-A and had the same sequence as pYGAIC3, except for the modified part.

EXAMPLE 5

Culture of Yeast Strain Transformed with an Expression Plasmid Encoding Insulin Precursor of the Invention

*Saccharomyces cerevisiae* strains transformed with the constructed plasmids were used.

Each strain was cultured on Petri plates containing minimal medium without uracil for 48 hours at 30° C. 100 ml shake bottles, containing minimal medium without uracil+5 g/liter casamino acids+10 g/liter succinic acid+30 g/liter glucose, pH 5.0, were then inoculated with a single colony from the Petri plate. The bottles were shaken for 72 hours at 30° C. in an incubator at 180 rpm.

A density corresponding to about 5 g/liter cell dry matter was obtained.

EXAMPLE 6

Isolation of Precursor from the Culture Supernatant

After centrifugation 5 liters culture supernatant was sterilized by filtration and adjusted by addition of distilled water and 5 M HCl to a conductivity of 8 mS and pH 4.5. The supernatant was then applied to a column (2.6×6.7 cm) of Pharmacia "FFS Sepharose" ® equilibrated with 10 bed volumes buffer (50 mM acetic acid in 50% ethanol adjusted to pH 4.0 with NaOH). The supernatant was applied to the column at a flow rate of 5.3 ml·min$^{-1}$ by use of a pump and the column was washed with 5 bed volumes of buffer. After washing of the column the insulin precursor was eluted by a linear gradient of NaCl from 0 to 350 mM in 30 bed volumes of the same buffer at a flow rate of 25 ml·hour$^{-1}$ and fractions of 10 ml were collected. Fractions containing precursor were identified by UV-absorbance and RP-HPLC analysis and were pooled. The pooled fractions were desalted on a column of "Sephadex" ® G25 adjusted with 1M acetic acid. The precursor was then isolated by lyophilization.

Identification of Isolated Insulin Precursors

Samples of the lyophilized precursors were hydrolysed in 6M HCl at 110° C. in sealed glass ampoules and analysed for amino acid compositon by use of an "LKB Alpha plus" amino acid analyzer. Samples of insulin precursors were also analysed by amino acid sequencing on an automatical amino acid sequencing system (Applied Bio System Model 477A) with online HPLC identification of amino acids.

The results confirmed that the connecting peptides were in accordance with the stated sequences.

Digestion of Insulin Precursor by Trypsin to Des(B30)-Insulin

The precursor was dissolved to a concentration of 2 mg/ml in 50 mM Tris, 20% ethanol adjusted to pH 10.0 with 1M HCl. The reaction was initiated by addition of 400 mg drained Sepharose gel containing 0.3 mg immobilized trypsin. The reaction was carried out at 4° C. with gentle agitation normally for 12 hours. The reaction was stopped by filtration of the mixture. The fermentation yields expressed in percent of the yield of the closely related known insulin precursor B(1-29)-Thr-Lys-Arg-A(1-21) are shown in the following table together with the efficiency of the digestion of precursors of the invention and the formation of by-products.

TABLE

| Connecting peptide between B(1-29) and A(1-21) | Yield of fermentation in % of yield of Thr—Lys—Arg | Yield of digestion in % of precursor | A$_0$Arg-Des-(B30)insulin or A$_0$Lys-des-(B30)insulin precursor |
|---|---|---|---|
| Thr—Lys—Arg | 100 | 70 | 27% |
| Leu—Asp—Lys—Arg | 64 | 84 | ~0 |
| Leu—Asp—Lys—Lys | 53 | 80 | ~0 |
| Leu—Glu—Lys—Arg | 64 | 76 | ~0 |
| Asp—Lys—Arg | 166 | 77 | ~0 |
| Glu—Lys—Arg | 286 | 78 | ~10 |

From the above table it appears that by conversion of the insulin precursors of the invention considerably higher yields of des-(B30)insulin are Obtained by enzymatic digestion than in the case of the closely related known precursor B(1-29)-Thr-Lys-Arg-A(1-21). Furthermore the preferred insulin precursors are expressed in much higher yields in yeast.

EXAMPLE 7

Isolation of Des(B30)-Insulin from Reaction Mixture

The reaction mixture was filtered and subjected to iso-electrical precipitation and lyophilization.

50 mg lyophilized substance was dissolved in 2 ml buffer (20 mM Tris, 7M urea adjusted to pH 8.1 with 1M NaOH) and applied to a column (1.6×20 cm) of Pharmacia "FFQ-Sepharose" ® anion exchanger adjusted with 10 column volumes buffer. The column was then eluted with a linear gradient of NaCl from 0 to 50 mM NaCl in 10 column volumes of the same buffer with a flow rate of 10 ml per hour. Fractions of 5 ml were collected. The positive fractions were identified by UV-absorbance and RP-HPLC analysis and were pooled. Des-B(30)-insulin was typically obtained in a yield of 75% after af final desalting on a column of "G25 Sephadex" ® in 1M acetic acid and lyophilization.

The identity of the compound was confirmed by amino acid analysis as described in example 6.

The amount of insulin precursor and of des(B30)insulin were determined by RP-HPLC analysis as described in B. S. Welinder/F. H. Andresen: Proceedings of the FDA-USP Workshop on Drugs and Reference Standards for Insulin, Somatotropins and Thyroid-axis Hormones. Bethesda, Md., May 19-21, 163-176 (1982).

The buffer system was composed of an A-buffer (0.125M ammonium sulphate 22.5% (vol/vol) acetonitril adjusted to pH 4.0 with sulphuric acid) and a B-buffer (0.125M ammonium sulphate 45% acetonitril adjusted to pH 4.0 with sulphuric acid). The column was a Hibar Lichrosorp RP-18, 5μ, 250×4 mm, which was eluted with a flow rate of 1.5 ml per minute. Samples containing des(B30)insulin were eluted with a gradient system recommended by Welinder and Andresen (1982), whereas samples containing insulin precursors were eluted with a linear gradient from 0 to 35% B-buffer increasing 1% per minute. The concentration was determined by comparison with a standard solution of the authentic insulin precursor.

We claim:

1. Insulin precursor having the amino acid sequence $B(1\text{-}29)\text{-}Asp\text{-}Lys\text{-}Arg\text{-}A(1\text{-}21)$ wherein B(1-29) are the 29 first amino acid residues of the B chain of human insulin starting from the N-terminus, A(1-21) are the 21 amino acid residues of the A chain of human insulin, the positions A6 and A11, A7 and B7 and A20 and B19, respectively, are connected through sulphur bridges, and, optionally, one or more of the glutamic acid residues in the positions A4, A17, B13 and B21 are substituted by another naturally-occurring alpha-amino acid residue having an uncharged side chain.

2. Insulin precursor of claim 1 wherein one or more of the glutamic acid residues in the positions A4, A17, B13 and B21 are substituted by another naturally-occurring alpha-amino acid residue having an uncharged side chain.

3. Insulin precursor having the amino acid sequence $B(1\text{-}29)\text{-}Glu\text{-}Lys\text{-}Arg\text{-}A(1\text{-}21)$ wherein B(1-29) are the 29 first amino acid residues of the B chain of human insulin starting from the N-terminus, A(1-21) are the 21 amino acid residues of the A chain of human insulin, the positions A6 and A11, A7 and B7 and A20 and B19, respectively, are connected through sulphur bridges, and, optionally, one or more of the glutamic acid residues in the positions A4, A17, B13 and B21 are substituted by another naturally-occurring alpha-amino acid residue having an uncharged side chain.

4. Insulin precursor of claim 3, wherein one or more of the glutamic acid residues in the positions A4, A17, B13 and B21 are substituted by another naturally-occurring alpha-amino acid residue having an uncharged side chain.

5. Insulin precursor having the amino acid sequence $B(1\text{-}29)\text{-}X_1\text{-}X_2\text{-}Y_2\text{-}Y_1\text{-}A(1\text{-}21)$ wherein B(1-29) are the 29 first amino acid residues of the B chain of human insulin starting from the N-terminus, A(1-21) are the 21 amino acid residues of the A chain of human insulin, $X_1$ represents a peptide bond or one naturally-occurring alpha-amino acid residue, $X_2$ represents Glu or Asp, and $Y_1$ and $Y_2$ each represents Lys or Arg, the positions A6 and A11, A7 and B7 and A20 and B19, respectively, are connected through sulphur bridges, and, optionally, one or more of the glutamic acid residues in the positions A4, A17, B13 and B21 are substituted by another naturally-occurring alpha-amino acid residue having an uncharged side chain.

6. Insulin precursor of claim 5 wherein one or more of the glutamic acid residues in the positions A4, A17, B13 and B21 are substituted by another naturally-occurring alpha amino acid residue having an uncharged side chain.

* * * * *